(12) United States Patent
Grillo-López

(10) Patent No.: US 6,455,043 B1
(45) Date of Patent: Sep. 24, 2002

(54) COMBINATION THERAPIES FOR B-CELL LYMPHOMAS COMPRISING ADMINISTRATION OF ANTI-CD20 ANTIBODY

(75) Inventor: Antonio J. Grillo-López, Rancho Sante Fe, CA (US)

(73) Assignee: IDEC Pharmaceuticals Corporation, San Diego, CA (US)

( * ) Notice: Subject to any disclaimer, the term of this patent is extended or adjusted under 35 U.S.C. 154(b) by 0 days.

(21) Appl. No.: 09/372,202

(22) Filed: Aug. 11, 1999

Related U.S. Application Data

(60) Provisional application No. 60/096,180, filed on Aug. 11, 1998.

(51) Int. Cl.[7] .................... A61K 39/395; A61K 51/00
(52) U.S. Cl. ........................... 424/155.1; 424/133.1; 424/143.1; 424/144.1; 424/156.1; 424/174.1; 424/1.49
(58) Field of Search .............................. 424/1.49, 133.1, 424/143.1, 144.1, 156.1, 174.1, 153.1; 530/387.3, 388.22, 388.73, 388.8, 388.85, 391.3

(56) References Cited

U.S. PATENT DOCUMENTS 5,595,721 A * 1/1997 Kaminski et al. .......... 424/1.49
5,736,137 A * 4/1998 Anderson et al. ........ 424/133.1

* cited by examiner

*Primary Examiner*—Michael G. Hartley
(74) *Attorney, Agent, or Firm*—Robin L. Teskin

(57) ABSTRACT

New combined therapeutic regimens for treatment of B-cell lymphomas are disclosed which comprise in particular administration of anti-CD20 antibodies to patients having low-, intermediate- or high-grade non-Hodgkins lymphomas.

15 Claims, No Drawings

COMBINATION THERAPIES FOR B-CELL LYMPHOMAS COMPRISING ADMINISTRATION OF ANTI-CD20 ANTIBODY

CROSS-REFERENCE TO RELATED APPLICATION

This application take priority from Provisional Application No. 60/096,180, filed on Aug. 11, 1998; the entire content of which is hereby incorporated by reference.

1. Field of the Invention

The invention relates to the use of anti-CD20 antibodies or fragments thereof in the treatment of B-cell lymphomas, particularly the use of such antibodies and fragments in combined therapeutic regimens.

2. Background of the Invention

The use of antibodies to the CD20 antigen as diagnostic and/or therapeutic agents for B-cell lymphoma has previously been reported. CD20 is a useful marker or target for B-cell lymphomas as this antigen is expressed at very high densities on the surface of malignant B-cells, i.e., B-cells wherein unabated proliferation can lead to B-cell lymphomas.

CD20 or Bp35 is a B-lymphocyte-restricted differentiation antigen that is expressed during early pre-B-cell development and remains until plasma cell differentiation. It is believed by some that the CD20 molecule may regulate a step in the B-cell activation process which is required for cell cycle initiation and differentiation. Moreover, as noted, CD20 is usually expressed at very high levels on neoplastic ("tumor") B-cells. The CD20 antigen is appealing for targeted therapy, because it does not shed, modulate, or internalize.

Previous reported therapies involving anti-CD20 antibodies have involved the administration of a therapeutic anti-CD20 antibody either alone or in conjunction with a second radiolabeled anti-CD20 antibody, or a chemotherapeutic agent.

In fact, the Food and Drug Administration has approved the therapeutic use of one such anti-CD20 antibody, Rituxan®, for use in relapsed and previously treated low-grade non-Hodgkin's lymphoma (NHL). Also, the use of Rituxan® in combination with a radiolabeled murine anti-CD20 antibody has been suggested for the treatment of B-cell lymphoma.

However, while anti-CD20 antibodies and, in particular, Rituxan® (U.S.; in Britain, MabThera®; in general Rituximab®), have been reported to be effective for treatment of B-cell lymphomas, such as non-Hodgkin's lymphoma, the treated patients are often subject to disease relapse. Therefore, it would be beneficial if more effective treatment regimens could be developed. More specifically, it would be advantageous if anti-CD20 antibodies had a beneficial effect in combination with other lymphoma treatments, and if new combined therapeutic regimens could be developed to lessen the likelihood or frequency of relapse. Also, it would be helpful if current treatment protocols for B-cell lymphoma were improved whereby patients with lymphomas which are refractory to other treatment methods could be treated with chimeric or radiolabeled anti-CD20 antibodies. It would also be helpful if treatment with anti-CD20 antibodies, particularly in combination with other treatments, could be used as therapy for other types of lymphoma besides low grade, follicular non-Hodgkins lymphoma (NHL).

SUMMARY OF THE INVENTION

The present invention discloses combined therapeutic treatments for B-cell lymphomas, and reports the benefits of treating relapsed or refractory B-cell lymphomas with chimeric and radiolabeled anti-CD20 antibodies. In particular, it has been found that treatment with anti-CD20 antibody provides a beneficial synergistic effect when administered in combination with cytokines, radiotherapy, myeloablative therapy, or chemotherapy. Surprisingly, patients who had prior bone marrow or stem cell transplantation had an unexpected increase in the over-all response rate when compared with patients with no prior therapy.

DETAILED DESCRIPTION OF THE INVENTION

This invention encompasses combined therapeutic regimens for the treatment of B-cell lymphomas. In general, such methods include a method for treating relapsed B-cell lymphoma, where a patient having prior treatment for lymphoma has relapsed and is administered a therapeutically effective amount of a chimeric anti-CD20 antibody. Such prior treatments can include, for example, previous treatment with anti-CD20 antibodies, treatments which included a bone marrow or stem cell transplantation, radiotherapy and chemotherapy. The previous chemotherapy may be selected from a wide group of chemotherapeutic agents and combination regimens, including CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP.

Also included in the methods of the invention are methods for treating a subject having B-cell lymphoma wherein the subject is refractory for other therapeutic treatments, including all those listed above, i.e., treatment with chimeric anti-CD20 antibody, treatments which included a bone marrow or stem cell transplantation, radiotherapy and chemotherapy. In particular, encompassed are methods of treating a patient who has not exhibited appreciable tumor remission or regression after administration of a chimeric anti-CD20 antibody, comprising administering to said patient a radiolabeled anti-CD20 antibody.

In particular, the methods of treating a patient with a radiolabeled antibody after a chimeric antibody are performed whereby the radiolabeled anti-CD20 antibody is administered from about one week to about two years after said administration of said chimeric anti-CD20 antibody. More particularly, the radiolabeled anti-CD20 antibody is administered from about one week to about nine months after said administration of said chimeric anti-CD20 antibody.

While any anti-CD20 antibodies can be used for the methods of the present invention, a preferred chimeric antibody is C2B8 (IDEC Pharmaceuticals, Rituximab®), A preferred radiolabeled antibody is Y2B8, which is a murine antibody labeled with yttrium-90 ($^{90}Y$). However, antibodies with other radiolabels may be used, particularly those labeled with a beta or alpha isotope. Anti-CD19 antibodies may also be used.

One of skill in the art would know the parameters for choosing a particular type of anti-CD20 antibody. For instance, chimeric and humanized antibodies are beneficial for decreased immunogenicity, and for facilitating antibody effector mediated immune reactions via the human constant region domains. Murine and other mammalian antibodies, in contrast, are beneficial for delivering a radiolabel to the tumor cell, as such antibodies generally have a decreased half-life in vivo.

Antibody treatments performed initially to which patients are refractory or have relapsed may include initial treatments with chimeric antibodies or mammalian antibodies. Also encompassed are initial treatments with other antibodies, including anti-CD19 antibodies and anti-Lym antibodies, and treatments with antibodies labeled with cytotoxic moieties, such as toxins, and radiolabels, e.g., Oncolym® (Techniclone) or Bexxar (Coulter).

It should be clear that the combined therapeutic regimens of the present invention can be performed whereby said therapies are given simultaneously, i.e., the anti-CD20 antibody is administered concurrently or within the same time frame (i.e., the therapies are going on concurrently, but the agents are not administered precisely at the same time). The anti-CD20 antibodies of the present invention may also be administered prior to or subsequent to the other therapies. Sequential administration may be performed regardless of whether the patient responds to the first therapy to decrease the possibility of remission or relapse.

The combined therapies of the present invention include a method for treating B-cell lymphoma comprising administering at least one chimeric anti-CD20 antibody and at least one cytokine. In particular, the invention includes a method for treating B-cell lymphoma comprising administering a synergistic therapeutic combination comprising at least one anti-CD20 antibody and at least one cytokine, wherein the therapeutic effect is better than the additive effects of either therapy administered alone. Preferred cytokines are selected from the group consisting of alpha interferon, gamma interferon, IL-2, GM-CSF and G-CSF. Again, the anti-CD20 antibody and the cytokine(s) may be administered sequentially, in either order, or in combination.

Also included in the present invention is a method for treating B-cell lymphoma comprising administering to a patient a therapeutically effective amount of a chimeric anti-CD20 antibody before, during or subsequent to a chemotherapeutic regimen. Such a chemotherapy regimen may be selected from the group consisting of, at the very least, CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP.

Also encompassed are methods for treating B-cell lymphoma comprising administering to a patient a therapeutically effective amount of a chimeric anti-CD20 antibody before, during or subsequent to a bone marrow or peripheral stem cell transplant. Such bone marrow transplant may also be accompanied by other therapeutic regimens such as chemotherapy. The antibodies of the present invention may also be used in a method of reducing residual CD20+ tumor cells in bone marrow or stem cells before or after myeloablative therapy by administering to a patient a chimeric anti-CD20 antibody. It may also be possible to use such antibodies in vitro to induce apoptosis of tumor cells and reduce or cure bone marrow or stem cell preparations of residual tumor cells before they are infused back into the patient.

It should be understood that stem cell transplants may be allogeneic or autologous. If the transplant is allogeneic, i.e., from another person, the disclosed therapeutic regimens may include treatments with immunosuppressive drugs before administration of the anti-CD20 antibodies. Coadministration of other drugs designed to enhance acceptance of the transplant and stimulate the production and differentiation of immune cells is also contemplated. For instance, it has been shown that administration of GM-CSF to marrow transplant recipients promotes the development of specific bone marrow cells which in turn produces circulating infection-fighting neutrophils, and increased the survival rate of marrow transplant recipients.

The methods of the present invention may be used to treat a variety of B-cell lymphomas, including low grade/follicular non-Hodgkin's lymphoma (NHL), small lymphocytic (SL) NHL, intermediate grade/follicular NHL, intermediate grade diffuse NHL, high grade inimunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention.

For instance, a recent classification system proposed by European and American pathologists is called the Revised European American Lymphoma (REAL) Classification. This classification system recognizes Mantle cell lymphoma and Marginal cell lymphoma among other peripheral B-cell neoplasms, and separates some classifications into grades based on cytology, i.e., small cell, mixed small and large, large cell. It will be understood that all such classified lymphomas may benefit from the combined therapies of the present invention.

The U.S. National Cancer Institute (NCI) has in turn divided some of the REAL classes into more clinically useful "indolent" or "aggressive" lymphoma designations. Indolent lymphomas include follicular cell lymphomas, separated into cytology "grades," diffuse small lymphocytic lymphoma/chronic lymphocytic leukemia (CLL), lymphoplasmacytoid/Waldenstrom's Macroglobulinemia, Marginal zone lymphoma and Hairy cell leukemia. Aggressive lymphomas include diffuse mixed and large cell lymphoma, Burkitt's lymphoma/diffuse small non-cleaved cell lymphoma, Lymphoblastic lymphoma, Mantle cell lymphoma and AIDS-related lymphoma. These lymphomas may also benefit from the combined therapeutic regimens of the present invention.

Non-Hodgkin's lymphoma has also been classified on the basis of "grade" based on other disease characteristics including low-grade, intermediate-grade and high-grade lymphomas. Low-grade lymphoma usually presents as a nodal disease, and is often indolent or slow-growing. Intermediate- and high-grade disease usually presents as a much more aggressive disease with large extranodal bulky tumors. Intermediate- and high-grade disease, as well as low grade NHL, may benefit from the combined therapeutic regimens of the present invention.

The Ann Arbor classification system is also commonly used for patients with NHL. In this system, stages I, II, III, and IV of adult NHL can be classified into A and B categories depending on whether the patient has well-defined generalized symptoms (B) or not (A). The B designation is given to patients with the following symptoms: unexplained loss of more than 10% body weight in the 6 months prior to diagnosis, unexplained fever with temperatures above 38° C. and drenching night sweats. Occasionally, specialized staging systems are used:

Stage I—involvement of a single lymph node region or localized involvement of a single extralymphatic organ or site.

Stage II—involvement of two or more lymph node regions on the same side of the diaphragm or localized involvement of a single associated extralymphatic organ or site and its regional lymph nodes with or without other lymph node regions on the same side of the diaphragm.

Stage III—involvement of lymph node regions on both sides of the diaphragm, possibly accompanying localized involvement of an extralymphatic organ or site, involvement of the spleen, or both.

Stage IV—disseminated (multifocal) involvement of 1 or more extralymphatic sites with or without associated lymph node involvement or isolated extralymphatic organ involvement with distant (non-regional) nodal involvement.

For further details, see The International Non-Hodgkin's Lymphoma Prognostic Factors Project: A predictive model for aggressive non-Hodgkin's lymphoma. New England J. Med. 329(14): 987–994 (1993).

Preferred antibodies, dosage regimens and particular combinations of therapy will now be illustrated by way of the following exemplary data.

Rituximab® and Y2B8

Non-Hodgkin's lymphoma (NHL) affects approximately 250,000 people in the United States. The majority of patients with NHL are not cured by chemotherapy, radiotherapy, or high-dose treatment with autologous bone marrow (ABMT) or peripheral blood stem cell (PBSC) support.

Approximately 80% of non-Hodgkin's lymphomas are B-cell malignancies and <95% of these express the CD20 antigen on the cell surface. This antigen is an attractive target for immunotherapy because it is found exclusively on B-cells, and not on hematopoietic stem cells, pro-B-cells, normal plasma cells, or other normal tissues. It is not shed from the cell surface and does not modulate upon antibody binding (1).

Rituximab® is one of a new generation of monoclonal antibodies developed to overcome limitations encountered with murine antibodies, including short half-life, limited ability to stimulate human effector functions, and immunogenicity (2,3).

Rituximab® is a genetically engineered monoclonal antibody with murine light- and heavy-chain variable regions and human gamma I heavy-chain and kappa light-chain constant regions. The chimeric antibody is composed of two heavy chains of 451 amino acids and two light chains of 213 amino acids and has an approximate molecular weight of 145 kD. Rituximab® is more effective than its murine parent in fixing complement and mediating ADCC, and it mediates CDC in the presence of human complement (4). The antibody inhibits cell growth in the B-cell lines FL-18, Ramos, and Raji, sensitizes chemoresistant human lymphoma cell lines to diphtheria toxin, ricin, CDDP, doxorubicin, and etoposide, and induces apoptosis in the DHL-4 human B-cell lymphoma line in a dose-dependent manner (5). In humans, the half-life of the antibody is approximately 60 hours after the first infusion and increases with each dose to 174 hours after the fourth infusion. The immunogenicity of the antibody is low; of 355 patients in seven clinical studies, only three (<1%) had a detectable anti-chimeric antibody (HACA) response.

Rituximab® was genetically engineered using the murine 2B8 antibody. The 2B8 antibody has also been conjugated to different radiolabels for diagnostic and therapeutic purposes. To this end, copending application Ser. Nos. 08/475,813, 08/475,815 and 08/478,967, herein incorporated by reference in their entirety, disclose radiolabeled anti-CD20 conjugates for diagnostic "imaging" of B-cell lymphoma tumors before administration of therapeutic antibody. "In2B8" conjugate comprises a murine monoclonal antibody, 2B8, specific to human CD20 antigen, that is attached to Indium[111] ($^{111}$In) via a bifunctional chelator, i.e., MX-DTPA (diethylene-triaminepentaacetic acid), which comprises a 1:1 mixture of 1-isothiocyanatobenzyl-3-methyl-DTPA and 1-methyl-3-isothiocyanatobenzyl-DTPA. Indium-[111] is selected as a diagnostic radionuclide because it emits gamma radiation and finds prior usage as an imaging agent.

Patents relating to chelators and chelator conjugates are known in the art. For instance, U.S. Pat. No. 4,831,175 of Gansow is directed to polysubstituted diethylenetriamine-pentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

The specific bifunctional chelator used to facilitate chelation in application Ser. Nos. 08/475,813, 08/475,815 and 08/478,967 was selected as it possesses high affinity for trivalent metals, and provides for increased tumor-to-non-tumor ratios, decreased bone uptake, and greater in vivo retention of radionuclide at target sites, i.e., B-cell lymphoma tumor sites. However, other bifunctional chelators are known in the art and may also be beneficial in tumor therapy.

Also disclosed in application Ser. Nos. 08/475,813, 08/475,815 and 08/478,967 are radiolabeled therapeutic antibodies for the targeting and destruction of B-cell lymphomas and tumor cells. In particular, the Y2B8 conjugate comprises the same anti-human CD20 murine monoclonal antibody, 2B8, attached to yttrium-[90] ($^{90}$Y) via the same bifunctional chelator. This radionuclide was selected for therapy for several reasons. The 64 hour half-life of $^{90}$Y is long enough to allow antibody accumulation by the tumor and, unlike e.g. $^{131}$I, it is a pure beta emitter of high energy with no accompanying gamma irradiation in its decay, with a range of 100 to 1000 cell diameters. The minimal amount of penetrating radiation allows for outpatient administration of $^{90}$Y-labeled antibodies. Furthermore, internalization of labeled antibodies is not required for cell killing, and the local emission of ionizing radiation should be lethal for adjacent tumor cells lacking the target antigen.

Because the $^{90}$Y radionuclide was attached to the 2B8 antibody using the same bifunctional chelator molecule MX-DTPA, the Y2B8 conjugate possesses the same advantages discussed above, e.g., increased retention of radionuclide at a target site (tumor). However, unlike $^{111}$In, it cannot be used for imaging purposes due to the lack of gamma radiation associated therewith. Thus, a diagnostic "imaging" radionuclide, such as $^{111}$In, can be used for determining the location and relative size of a tumor prior to and/or following administration of therapeutic chimeric or $^{90}$Y-labeled antibodies in the combined regimens of the invention. Additionally, indium-labeled antibody enables dosimetric assessment to be made.

Depending on the intended use of the antibody, i.e., as a diagnostic or therapeutic reagent, other radiolabels are known in the art and have been used for similar purposes. For instance, radionuclides which have been used in clinical diagnosis include $^{131}$I, $^{125}$I, $^{123}$I, $^{99}$Tc, $^{67}$Ga, as well as $^{111}$In. Antibodies have also been labeled with a variety of radionuclides for potential use in targeted immunotherapy (Peirersz et al. (1987) The use of monoclonal antibody conjugates for the diagnosis and treatment of cancer. *Immunol. Cell Biol* 65: 111–125). These radionuclides include $^{188}$Re and $^{186}$Re as well as $^{90}$Y, and to a lesser extent $^{199}$Au and $^{67}$Cu. I-(131) has also been used for therapeutic purposes. U.S. Pat. No. 5,460,785 provides a listing of such radioisotopes and is herein incorporated by reference.

As reported in copending application Ser. Nos. 08/475,813, 08/475,815 and 08/478,967, administration of the radiolabeled Y2B8 conjugate, as well as unlabeled chimeric anti-CD20 antibody, resulted in significant tumor reduction in mice harboring a B-cell lymphoblastic tumor. Moreover, human clinical trials reported therein showed significant B-cell depletion in lymphoma patients infused with chimeric anti-CD20 antibody. In fact, chimeric 2B8 has recently been heralded the nation's first FDA-approved anti-cancer monoclonal antibody under the name of Rituxan®. Thus, at least one chimeric anti-CD20 antibody has been shown to demonstrate therapeutic efficacy in the treatment of B-cell lymphoma.

In addition, U.S. Application Ser. No. 08/475,813, herein incorporated by reference, discloses sequential administration of Rituxan®, a chimeric anti-CD20, with both or either indium-labeled or yttrium-labeled murine monoclonal antibody. Although the radiolabeled antibodies used in these combined therapies are murine antibodies, initial treatment with chimeric anti-CD20 sufficiently depletes the B-cell population such that the HAMA response is decreased, thereby facilitating a combined therapeutic and diagnostic regimen.

Thus, in this context of combined immunotherapy, murine antibodies may find particular utility as diagnostic reagents. Moreover, it was shown in U.S. application Ser. No. 08/475,813 that a therapeutically effective dosage of the yttrium-labeled anti-CD20 antibody following administration of Rituxan® is sufficient to (a) clear any remaining peripheral blood B-cells not cleared by the chimeric anti-CD20 antibody; (b) begin B-cell depletion from lymph nodes; or (c) begin B-cell depletion from other tissues.

Thus, conjugation of radiolabels to cancer therapeutic antibodies provides a valuable clinical tool which may be used to assess the potential therapeutic efficacy of such antibodies, create diagnostic reagents to monitor the progress of treatment, and devise additional therapeutic reagents which may be used to enhance the initial tumor-killing potential of the chimeric antibody. Given the proven efficacy of an anti-CD20 antibody in the treatment of non-Hodgkin's lymphoma, and the known sensitivity of lymphocytes to radioactivity, it would be highly advantageous for such chimeric and radiolabeled therapeutic antibodies to find use in combined therapeutic regimens which decrease the frequency of relapsed or refractory non-Hodgkin's lymphoma. In addition, it would be beneficial if such combined therapeutic regimens found use in the treatment of other B-cell lymphomas.

LOW-GRADE OR FOLLICULAR NHL

Single-Agent Studies with Relapsed or Refractory NHL

FDA approval of Rituximab® was based on five single-agent studies primarily in patients with low-grade or follicular NHL. An early Phase I study of single Rituximab® infusions ranging from 10–500 mg/m$^2$ demonstrated that the maximum tolerated dose had not been reached; however, the length of infusion time at the highest dose was not considered feasible for outpatient therapy. The ORR in 15 patients was 13% (Table 1)(6).

TABLE 1

Rituximab ®: Summary of Efficacy Results

| Study Description | Indication | N* | ORR | CR | PR | Median DR (months) | Median TIP (months) | References |
|---|---|---|---|---|---|---|---|---|
| Phase I/II, Single-Dose Single Agent | Relapsed B-Cell Lymphoma | 15 | 2 (13%) | 0 (0%) | 2 (13%) | NA† | 8.1 | 6 |
| Phase I/II, Multiple-Dose Dose-Ranging | Relapsed Low-, Intermediate-, and High-Grade Lymphoma | 34 | 17 (50%) | 3 (9%) | 14 (41%) | 8.6 | 10.2 | 7 |
| Phase II; Multiple-Dose Combined with CHOP | Newly Diagnosed and Relapsed Low-Grade or Follicular B-Cell Lymphoma | 38 | 38 (100%) | 22 (58%) | 16 (42%) | 35.3+ | 36.7+ | 21, 22 |
| Phase III, Multiple-Dose Single-Agent | Relapsed Low-Grade or Follicular B-Cell Lymphoma | 151 | 76 (50%) | 9 (6%) | 67 (44%) | 11.6 | 13.2 | 8, 9 |
| Phase II, Multiple-Dose Single-Agent | Relapsed Low-Grade or Follicular B-Cell Lymphoma | 35 | 21 (60%) | 5 (14%) | 16 (46%) | 13.4+ | 19.4+ | 13 |
| Phase II, Multiple-Dose, Combined with Interferon | Relapsed Low-Grade or Follicular B-Cell Lymphoma | 38 | 17 (45%) | 4 (11%) | 13 (34%) | 22.3+ | 25.2+ | 29 |
| Phase II, Multiple-Dose, Single-Agent | Relapsed Low-Grade or Follicular B-Cell Lymphoma, Bulky Disease | 28 | 12 (43%) | 1 (4%) | 11 (39%) | 5.9 | 8.1 | 14 |
| Phase II, Multiple-Dose, Single-Agent | Relapsed Low-Grade or Follicular B-Cell Lymphoma, Retreatment | 57 | 23 (40%) | 6 (11%) | 17 (29%) | 15.0+ | 16.7+ | 19, 20 |
| Phase II, Multiple-Dose Combined with CHOP Modality | Previously Untreated Intermediate- or High-Grade Lymphoma | 30 | 29 (96%) | 19 (63%) | 10 (33%) | 11+ | 17+ | 34 |
| Phase II, Alternative Multiple Dosing | Intermediate- or High-Grade B-Cell Lymphoma | 54 | 17 (32%) | 5 (9%) | 12 (22%) | NA† | 8.2+ | 33 |

*N = number of evaluable patients
†Not available

In Phase I of a Phase I/II dose-ranging study, patients received 125–375 mg/m$^2$ administered as four weekly infusions. No dose-related toxicities were demonstrated, and 375 mg/m$^2$ was chosen as the Phase II dose. Tumor regressions were observed in 17 of 37 (46%) patients who received this dose, including 3 (8%) complete responses (CR) and 14 (38%) partial responses PR (7).

A subsequent single-arm pivotal study of Rituximab® infused at 375 mg/m² weekly times four was conducted in 166 patients with relapsed or refractory, low-grade or follicular NHL (International Working Formulation [IWF] Types A–D and REAL classification, small lymphocytic lymphoma, Follicular center, follicular Grades I, II, 111(8)). Patients with tumor masses >10 cm or with >5000 lymphocytes/μL in the peripheral blood were excluded from this study. The median age was 58 years (105 men and 61 women) and the median number of prior treatments was three. Bone marrow involvement was present in 56% of 149 patients evaluated. Forty-five percent had ≦2 extranodal sites and 41% had bulky disease (≦5 cm).

Complete response required the regression of all lymph nodes to <1×1 cm² demonstrated on two occasions at least 28 days apart on neck, chest, abdomen, and pelvic CT scans, resolution of all symptoms and signs of lymphoma, and normalization of bone marrow, liver, and spleen. Partial response required a ≦50% decrease in the sum of the products of perpendicular measurements of lesions without any evidence of progressive disease for at least 28 days. Patients who did not achieve a CR or PR were considered non-responders, even if a net decrease (>50%) of measurable disease was observed. Time to progression was measured from the first infusion until progression.

The overall response rate (ORR) was 48% with a 6% CR and a 42% PR rate(8). The median time to progression (TTP) for responders was 13.2 months and the median duration of response (DR) was 11.6 months. Twenty-two of 80 (28%) responders remain in ongoing remission at 20.9+ to 32.9+ months (9).

Administration of Rituximab® resulted in a rapid and sustained depletion of B-cells. Circulating B-cells were depleted within the first three doses with sustained depletion for up to six to nine months post-treatment in 83% of patients. Median B-cell levels returned to normal by 12 months following treatment. Although median NK cell counts remained unchanged, a positive correlation was observed between higher absolute NK cell counts at baseline and response to Rituximab® (10).

Several baseline prognostic factors were analyzed to determine their correlation to response. Significantly, in 23 patients relapsed after ABMT or PB SC, the ORR was 78% versus 43% in patients who did not undergo prior high-dose therapy (p<0.01). In a multivariate analysis, the ORR was higher in patients with follicular NHL as compared with small lymphocytic lymphoma (58% vs. 12%, p<0.01), and higher in patients with chemosensitive relapse as compared with chemoresistant relapse (53% vs. 36%, p=0.06). No effect on response rate was associated with: age >60 years, extranodal disease, prior anthracycline therapy, or bone marrow involvement.

A statistically significant correlation was found between the median serum antibody concentration and response at multiple time points during treatment and follow up (11).

Serum levels of antibody were higher in patients with follicular NHL compared with small lymphocytic lymphoma. Mean serum antibody was also inversely correlated with measurements of tumor bulk and with the number of circulating B-cells at baseline. The association of lower serum antibody concentrations with higher numbers of circulating NHL cells and with higher tumor bulk suggest that the main mode of antibody clearance is to tumor cells. The association of high serum antibody concentrations with response and lower tumor bulk or circulating cells suggests that higher or more doses of Rituximab® may be necessary to induce responses in some subsets of patients, such as those with bulky disease.

Nevertheless, responses were seen with Rituximab® in 43% of patients with tumors >5 cm and in 35% of patients with tumors >7 cm, suggesting that treatment of patients with bulky disease with Rituximab® is feasible. This is surprising considering it was long thought that antibody therapy is not conducive to treating bulky disease due to the compact nature of the tumors.

In a study conducted in Japan (12), patients with relapsed B-cell lymphoma were treated with either 250 mg/m²(N=4) or 375 mg/m²(N=8) of Rituximab® weekly times four. Of 11 evaluable patients, 8 had follicular NHL, 2 had diffuse large-cell NHL, and one had mantle-cell lymphoma. Two of the 11 had a CR and 5 had a PR for an ORR of 64%; all responders had follicular histology.

Because Rituximab® serum levels and response were positively correlated in previous studies, a Phase II study of eight weekly doses of 375 mg/m² Rituximab® was conducted in low-grade or follicular NHL patients. The ORR was 60% in evaluable patients, with a 14% CR and a 46% PR rate. Median values for TTP in responders and DR were 13.4+ months and 19.4+ months, respectively (13). Though it is difficult to compare across studies, it appears that TTP and DR may be improved by using more doses.

Contrary to early assumptions about antibody therapy being useful only in micrometastatic disease, Rituximab® is quite active in high bulk disease. In a separate study, 31 patients with relapsed or refractory, bulky low-grade NHL (single lesion of >10 cm in diameter) received 375 mg/m² Rituximab® as four weekly infusions. Twelve of 28 evaluable patients (43%) demonstrated a CR (1, 4%) or PR (11, 39%)(14).

Waldenstrom's Macroglobulinemia

Waldenstrom's Macroglobulinemia (WM) is a malignancy wherein B lymphocytes secrete excessive amounts of IgM antibodies. WM usually occurs in people over sixty, but has been detected in adults in their early thirties. WM today is considered a rare incurable indolent malignancy, which has in the past been treated by plasmaphoresis to reduce serum viscosity. Chemotherapeutic drugs such as an alkylating agent and a corticosteroid are often prescribed. The most recommended drug for WM has been Leustatin (2CdA).

A report on seven patients with Waldenstrom's macroglobulinemia where the patients were treated with Rituximab® (375 mg/m² weekly times 4)(15) noted responses in 4 (57%) of patients. Median progression-free survival was 8 months (range 3–27+ months). Thus, Rituximab® should be useful in combined therapeutic protocols, particularly with chemotherapeutic reagents such as 2CdA.

Chronic Lymphocytic Leukemia (CLL)

CLL is the liquid (leukemic) equivalent of small lymphocytic lymphoma (SLL). Patients with SLL had lower serum levels and a lower response rate when treated with the standard dose of Rituximab® than patients with other low-grade NHL subtypes. This is probably due to the very high levels of circulating tumor cells in patients with CLL, and because malignant cells involved in CLL are thought to have reduced levels of expression of CD20 on the cell surface.

Nevertheless, the present inventors have discovered that hematologic malignancies such as CLL may be treated with Rituximab®. A recent clinical study evaluated treatment of CLL patients at higher doses of Rituximab® (16). All patients receive a first dose of 375 mg/m³ to minimize infusion-relapsed side effects. Subsequent weekly dosages (3) remained the same but were given at an increased dose level. Sixteen patients have been treated at dosages of 500–1500 mg/m³. Medium age was 66 years (range, 25–78).

Eighty-one percent had end-stage III-IV disease. Medium white blood cell count was $40 \times 10^9$/L (range, 4–200), Hgb 11.6 g/dl (range, 7.7–14.7), platelets $75 \times 10^9$/L (range, 16–160), median $\beta_2$ imunoglobulin was 4.5 mg/L (range, 3.1–9.2). Median numbers of prior therapies was 2.5 (range 1–9). Sixty percent of patients were refractory to treatment. Two patients developed severe hypertension with the first dose (375 mg/m$^3$); another one received further therapy. Toxicity at subsequent escalated dosages has been mild although no patient at the 1500 mg/m$^3$ dose level has been fully evaluated. Eight patients have completed therapy (4 at 500 mg/m$^3$, 3 at 650 mg/m$^3$, 1 at 825 mg/m$^3$). On patient treated at 560 mg/m$^3$ achieved full remission. One patient has progressive lympocytosis on treatment and all other patients had reduction in peripheral blood lymphocytosis but less effect on lymph nodes. Dose escalation studies are ongoing.

Another approach to improving response in CLL patients is to upregulate the CD20 antigen using cytokines. In an in vivo study, mononuclear cells from CLL patients were incubated for 24 hours with various cytokines. Flow cytometry results showed significant up-regulation by IL-4, GM-CSF, and TNF-alpha (17). In fact, recent data suggests that the upregulation of CD20 observed on CLL cells may be limited to tumor cells (Venogopal et al. Poster—PanPacific Lymphoma meeting, June 1999. Cytokine-induced upregulation of CD20 antigen expression in chronic lymphocyfic leukemia (CLL) cells may be limited to tumor cells). Preliminary data also suggest that interferon alpha also upregulates CD20 on CLL cells after only 24 hours when applied at a concentration of 500 to 1000 U/ml.

Thus, by administering certain cytokines to CLL patients prior to or concurrently with administration of Rituximab®, the expression of CD20 on the surface of malignant B-cells may be upregulated, thereby rendering CD20, as well as other cell surface markers such as CD19, a more attractive target for immunotherapy. A collaborative study has been initiated to test for optimal cytokine doses for CD20 upregulation in vivo. The study protocol involves treating ten patients initially with GM-CSF at 250 mcg/m$^2$ SQ QD X 3, ten patients with IL-4 mcg/kg SQ QD X 3, and ten patients with G-CSF at 5 mcg/kg SQ QD X 3. Mononuclear cells will be separated by Ficon Hypaque centrifugation for apoptotic studies to determine if upregulation of CD20 translates to enhanced killing of tumor cells by Rituximab®.

Antibody treatment of CLL can be combined with other conventional chemotherapeutic treatments known to be useful for the treatment of CLL. The most frequently used single agent for CLL is chlorambucil (leukeran), given either as 0.1 mg/kg daily or 0.4 to 1.0 mg/kg every 4 weeks. Chlorambucil is often combined with oral prednisone (30 to 100 mg/m$^2$/d), which is useful in the management of autoimmune cytopenias. Cyclophosphamide is an alternative to chlorambucil, the usual dose being 1–2 g/m$^2$ every 3–4 weeks together with vincristine and steroids (e.g., COP regimen).

Various drug combinations have been used for CLL, including COP (cyclophosphamide, Oncovin, and prednisone), and CHOP (these three drugs plus doxorubicin). Fludarabine has shown an effect in the treatment of CLL, and gave an ORR of 50% in a group of patients treated with 25–30 mg/m$^2$/d every 3–4 weeks. http://www.cancernetwork.com. Although some patients have been shown to be refractory for fludarabine. Such patients may also be resistant to 2-CdA because often, patients who are refractory to fludarabine are also refractory to 2-CDA (O'Brien et al. N. Engl. J. Med. 330: 319–322 (1994)).

Hence, anti-CD20 antibody therapy will be particularly useful for patients who are refractory or who have relapsed after treatment with chemotherapeutic drugs. Rituximab® therapy may also be combined with radiotherapy in these patients. TBI with a low fraction size of 15 cGy to total doses of 75 to 150 cGy has been shown to be effective in about one-third of patients.

A Phase II trial is currently being conducted by CALGB in CLL patients. Rituximab® and fludarabine are administered concurrently, followed by Rituximab® consolidation versus fludarabine induction followed by Rituximab®.

Rituximab® with Myeloablative Therapy

Myeloablative therapy has yielded responses in indolent lymphomas; however, residual tumor cells may remain despite high-dose therapy and the PBSC reinfused may contain tumor cells. Rituximab® is being used before stem cell mobilization and after transplant to reduce residual CD20+ tumor cells and contamination of the bone marrow or stem cells harvested. Interim results demonstrated that no CD20+ cells were detectable in harvested cells. Eighteen of 24 patients achieved engraftment and the treatment was well tolerated. PCR testing is ongoing to evaluate residual tumor cells (18).

Retreatment of Relapsed Low-Grade NHL with Rituximab®

A trial evaluating retreatment of 53 patients who had responded to Rituximab® and later relapsed has been reported (19). Seven of 56 evaluable patients (13%) obtained a CR and 16 a PR (29%), for an ORR of 42%. Four patients who had a second response received a third treatment; 3 of these responded.

After treatment with two courses of Rituximab®, one patient's tumor, initially classified as follicular, small cleaved cell NHL, no longer expressed the CD20 antigen and was unresponsive to Rituximab® at the time of transformation to diffuse, large-cell NHL (20).

Thus, while retreatment with Rituximab® is effective for treating patients who have relapsed after prior treatment with Rituxinab®, there may be an increased incidence of CD20-tumor cells after secondary treatment. This observation supports the utility of the combined therapeutic treatment regimens described herein.

Combination of Rituximab® and CHOP Chemotherapy for Low-Grade NHL

Chemotherapy with cyclophosphamide, doxorubicin, vincristine, and prednisone (CHOP) is an effective first-line therapy for low-grade or follicular NHL. Though initial response rates are high, relapse eventually occurs and subsequent chemotherapy regimens produce remissions with shorter durations. A Phase II trial was initiated to evaluate the combination of CHOP and Rituximab((21) in newly diagnosed and relapsed low-grade or follicular NHL because their mechanisms of action are not cross-resistant, and Rituximab® is synergistic with certain cytotoxic drugs, including doxorubicin (5).

Twenty-nine of 38 patients received no prior anticancer therapy. CHOP was administered at standard doses every three weeks for six cycles with six infusions of Rituximab® (375 mg/m$^2$). Rituximab® infusions 1 and 2 were administered on Days 1 and 6 before the first CHOP cycle, which started on Day 8. Rituximab® infusions 3 and 4 were given 2 days before the third and fifth CHOP cycles, respectively, and infusions 5 and 6 were given on Days 134 and 141, respectively, after the sixth CHOP cycle.

In this combination study, 100% of the 38 patients treated responded (CR, 58%; PR, 42%). Of 35 evaluable patients who completed treatment, there were 63% CR, and 37% PR(21). Median DR is 35.3+ months with median progression-free survival not reached after a median observation time of 36.7+ months. Twenty patients are still in remission after 36+ months to 53.4+ months (22). This DR is impressive even for first-line treatment, and 24% of this trial population had relapsed after chemotherapy.

In a study to be conducted by CALGB, 40 patients with low-grade NHL will receive Rituximab® weekly times 8 and oral cyclophosphamide daily starting on Day 8. Twenty patients will receive Rituximab® alone for 8 weekly doses.

A Phase III study conducted by ECOG in patients with low-grade NHL is comparing the combination of cyclophosphamide and fludarabine (Arm A) with standard CVP therapy (Arm B). In the randomization to Arm A or Arm B, patients are stratified by age, tumor burden, histology, and B symptoms. Responders in both arms will undergo a second randomization to Rituximab® maintenance therapy (375 mg/m$^2$ weekly times 4 every 6 months for 2 years (Arm C) or to observation (Arm D).

Combination of Rituximab® with Cytokines

Rituximab® Plus Interferon Alpha

Interferon is a cytokine involved in modulating the immune system (23). Mechanisms by which interferon may increase the effectiveness of antibodies include the potentiation of antigen expression (24), increased targeting of antibodies into tumors (25,26), and enhanced cytotoxicity of immunotoxins (27).

In a combination trial, interferon-alpha (Roferon-A), a cytokine with a single-agent clinical activity in NHL (28), and Rituximab® were given to patients with relapsed low-grade or follicular NHL. Interferon-alpha (2.5 or 5 MIU) was administered subcutaneously, three times weekly for 12 weeks. Rituximab® was administered by IV infusion weekly for four doses (375 mg/m$^2$) starting on the fifth week of treatment. The ORR was 45% (17/38 patients); 11% had a CR and 34% had a PR. Kaplan-Meier estimates of the median DR and TTP in responders were 22.3+ and 25.2+ months, respectively (29). Previous combination studies of interferon-alpha and chemotherapeutic regimens containing anthracyclines yielded prolonged time to progression, but did not consistently increase response or survival rates (30–32). These early results suggest that the combination of Rituximab® and interferon-alpha may prolong the time to progression relative to Rituximab® alone.

Rituximab® Plus G-CSF

In a separate study, Rituximab® and G-CSF are being evaluated in relapsed low-grade NHL. It has been demonstrated in vivo as well as in vivo in healthy volunteers that G-CSF, via its effect on myeloid precursor cells, induces FcRI-positive neutrophils that are capable of functioning as effector cells in ADCC. Therefor, a Phase I/II study was initiated to evaluate the toxicity and efficacy of the combined treatment.

Both in Phase I and Phase II, patients were administered a standard dose of G-CSF (5 µg/kg/day) administered for three days, starting 2 days before administration of Rituximab®. Phase I consisted of a dose escalation of Rituximab® (125, 250, or 375 mg/m$^2$ weekly X4). Early results in 9 patients evaluated so far yielded an ORR of 67% (44% CR, 22% PR) with minor toxicity in 8 of the 9 patients (33). The most frequent adverse events were fever (4/8 patients), rhinitis (4/8), chills (3/8) and headaches (3/8), which were comparable to the adverse events observed previously in administration of Rituximab® alone. The Phase II part of the study has been initiated, which will examine the efficacy of the combination of G-CSF and 375 mg/m$^2$ Rituximab® X4.

Rituximab® Plus IL-2

High-dose therapy with autologous peripheral blood stem cells (PBSC)or bone marrow (BM) rescue has been used to treat NHL, however success remains limited by the high risk of relapse, which is 50–80%. In an effort to improve durable remissions post-transplant, immunotherapy including high dose and low dose therapy with IL-2 has been studied in a number of treatment centers. Such studies have suggested that IL-2 therapy does demonstrate early post-transplant anti-Tumor activity.

Initially following autologous transplant, patients display delayed immune reconstitution which potentially results in diminished immune-mediated tumor eradication (43, 44). Indeed, it has been shown that both CD$+ T cells and cytotoxic CD8+ T cells are depressed (45–49). In vitro assays have demonstrated a profound suppression of T cell cytolytic and proliferative responses as well as decreased production of IL-2 in response to mitogens and soluble antigens. However, soluble IL-2 is able to restore these immune responses suggesting that immune cells in patients after autologous transplant are capable of responding to exogenous IL-2 (47). Peripheral blood NK activity also remains lower following BMT than control values and the NK activity is also augmented by addition of exogenous IL-2 (49). These data suggest that administration of IL-2 to patients shortly after stem cell transplant may enhance immune responsiveness at a critical period when tumor burden is minimal and when immune responsiveness in the absence of IL-2 is lacking.

For instance, Caligiuru et al. have shown that IL-2 (Hoffman-LaRoche) administered at 0.45×10$^6$ U/M$^2$/day by 24 hour CIV for 12 weeks was able to expand the absolute number of CD56 bright NK cells (50–52). This regimen was administered to non-transplant patients in the outpatient setting with little toxicity.

Animal models have shown that non-LAK inducing low doses of IL-2 dramatically enhances anti-tumor activity when administered with tumor-specific T effector cells (53). In addition, Soiffer et al. (54) administered low doses of IL-2 to 13 autologous BMT or T cell depleted allogeneic BMT recipients undergoing treatment for relapsed leukemia or lymphoma. Enhanced immunological responsiveness was demonstrated in the laboratory with a 5 to 40-fold increase in circulating CD56 bright CD16+ CD3– NK cells. Moreover, this low dose regimen of IL-2 resulted in augmented in vitro killing of the NK targets K562. When Soiffer et al. (55) updated the outcome of 29 allogeneic BMT patients who received low dose IL-2, they found superior survival for these patients (70%) compared to histological controls (30%, p=0.41).

Lauria et al. (56) treated 11 patients with high grade NHL at a median of 42 days after ABMT with IL-2 at a dose of 2×10$^6$ IU/m$^2$ qod for two weeks and then 3×10$^6$ IU/m$^2$ twice a week for a year. Phenotypic analysis showed a persistent and significant (p=0.001) increase in the proportion and absolute number of total lymphocytes and especially of both CD16 and CD56 NK cells after 6 months of therapy. None of the patients progressed with a median follow-up of twenty-two months (range 10–42 months) after starting therapy. In addition, two patients with residual disease after ABMT, one in the liver and second in the lymph nodes, obtained a complete response after 7 and 10 months of IL-2 therapy.

Vey et al. (57) treated 25 patients with refractory or relapsed HD (11 patients) and NHL (14 patients) with low dose IL-2. 48% of the patients had resistant disease at transplant and 84% achieved CR after ABMT. IL-2 was started at a mean of 54 days after transplant and consisted of a first cycle of 5 days followed by 4 cycles of 2 days every other week. Patients received a mean of 160×10$^6$ IU/m2 of IL-2. After a five year follow-up, the probability of survival and DFS is 72% (HD 73% and NHL 70%) and 45% (HD 36% and NHL 48%).

A group at the Fred Hutchinson Cancer Research Center (FHCRC) has recently found that low dose IL-2 therapy was well-tolerated in the outpatient setting, and that remissions in patients treated with low dose IL-2 tended to be longer than without IL-2 treatment. IL-2 therapy was associated with an increase in the number of certain populations of immune cells, including CD8+ CD69+ cells; CD 16+ CD8+ cells; CD16+ CD69+ cells; CD 16+ CD56+ cells; CD16+ CD 122+ cells; CD 16+ Dr+ cells; and CD8+ CD56+ cells. There was also an increase in the expression of lytic activity against the timor targets K562 and Daudi, with a median of 5.9-fold and 6.5-fold increase, respectively. Relapses, when they occurred, occurred at a median of 17.8 months after transplant, and therefor remissions were reported to be characteristically longer than what was historically seen in transplant recipients without IL-2 therapy.

Given the encouraging data gathered from single therapy studies with IL-2 on ABMT transplant recipients, it seemed reasonable to combine IL-2 therapy with Rituximab® post transplant, given that Rituximab's biological activity appears to be mediated through ADCC and complement-mediated lytic activity. Thus, a Phase I trial has been initiated in collaboration with the FHCRC to evaluate the safety and potential efficacy of a combined therapeutic regimen.

A separate Phase II study is also being performed to evaluate the efficacy and the incidence of HACA formation in patients receiving low-dose IL-2 and Rituxan®. A specific objective of this study is to assess whether ADCC is enhanced by in vivo exposure to IL-2 and whether ADCC activity correlates with clinical response. Inclusion criteria for patients are histologically confirmed stage II-IV low-grade, follicular B-cell or mantle cell ylmphoma. Mantle cell lymphoma, for the purposes of this clinical study, is defined as CD5+, CD23– (if available) and/or bcl-1+ by immuno-histochemistry. Patients who did not respond to or have relapsed following their first treatment with a standard therapy, i.e., chemotherapy, radiotherapy, ABMT and/or immunotherapy, are eligible.

Rituximab® Plus GM-CSF for the Treatment of Relapsed Low Grade or Follicular B-Cell Lymphoma Two separate Phase II trials have also been initiated to test the efficacy of combined treatment with Rituximab® and GM-CSF. One study involves 40 patients with relapsed low grade B-cell lymphoma, and comprises administering Rituximab® at 375 mg/m$^2$ weeklyx4 (d. 1, 8, 15, 22) and GM-CSF (Leukine, Immunex) at 250 mcg sc three times weekly for 8 weeks, starting one hour before the first dose of Rituximab®. This study will be used to evaluate the clinical efficacy (overall response rate (ORR), overall complete response rate, time to progression and failure-free survival) of the combined therapeutic regimen, to characterize the safety (qualitative, quantitative, duration and reversibility of adverse events) of the combined therapy, and to determine the effects of the combined therapy on relevant lymphocyte subsets and cytolines. The second study plans to also monitor immunologic parameters to assess the mechanism of killing (complement C3 and C4, CH50, flow cytometry for CD3, CD4, CD8, CD 16, CD 19 and CD56 and ADCC assay).

Rituximab® Plus Gamma-Interferon

Gamma-interferon may also be useful in combined therapy with Rituximab® for treating patients with low-grade or higher-grade lymphomas. It is has recently been found that gamma-interferon upregulates CD20 expression on multiple myeloma (MM) patient plasma cells, patient B-cells, as well as on normal donor B-cells (Treon et al., Lugano, 1999). In fact, Treon and colleagues have shown that gamma-interferon augments binding of these cells to Rituxinab®. Induction of CD20 expression on plasma cells occurred in a dose dependent manner, with upregulation seen with as little as 1 U/ml of interferon gamma. A plateau occurred at 100 U/ml at 48 hours. Thus, gamma-interferon may also be beneficial when administered in combination with Rituximab®.

INTERMEDIATE-GRADE AND HIGH-GRADE NHL

Single-Agent Studies

In a study conducted in Europe and Australia, alternative dosing schedules were evaluated in 54 relapsed or refractory intermediate- or high-grade NHL patients (34). Rituximab® was infused at 375 mg/m$^2$ weekly for 8 doses or at 375 mg/m2 once followed by 500 mg/m$^2$ weekly for 7 doses. The ORR was 31%; (CR 9%, PR 22%) no significant difference between the dosing regimens was observed. Patients with diffuse large-cell lymphoma (N=30) had an ORR of 37% and those with mantle-cell lymphoma (N=12) had an ORR of 33%.

Combination of Rituximab® and CHOP Chemotherapy

In another study, 31 patients with intermediate- or high-grade NHL (19 females, 12 males, median age 49) received Rituximab® on Day 1 of each of six 21-day cycles of CHOP (35). Of 30 evaluable patients, there were 19 CR (63%) and 10 PR (33%), for an ORR of 96%. This regimen was considered well tolerated and may result in higher response rates than with Rituximab® or CHOP alone.

The NCI Division of Cancer Treatment and Diagnosis is collaborating with IDEC Pharmaceuticals Corporation to explore Rituximab® treatment in other indications. A Phase II trial of CHOP versus CHOP and Rituximab® is being conducted by ECOG, CALGB, and SWOG in older patients (>60 years) with mixed, diffuse large cell, and immunoblastic large cell histology NHL (N=630 planned). This study includes a secondary randomization to maintenance with Rituximab® versus non-maintenance.

A Phase III trial of Rituximab® and CHOP in 40 patients with previously untreated mantle-cell lymphoma is also ongoing at the Dana Farber Institute. Rituximab® is administered on Day 1 and CHOP is given on Days 1–3 every 21 days for 6 cycles. Accrual for this study has been completed. A Phase II trial of CHOP followed by Rituximab® in newly diagnosed follicular lymphoma conducted by SWOG has also been completed. Results of these two trials are being analyzed.

A Phase II trial of CHOP and Rituximab® versus CHOP alone in HIV-related NHL conducted by the AIDS Malignancy Consortium is ongoing; 120 patients are planned.

Rituximab® After Myeloablative Therapy Relapse

Rituximab® has shown promising early results in patients with relapsed intermediate-grade NHL after high-dose therapy with autologous PBSC support. Six of seven patients responded (1 CR and 5 PR) and one patient had stable disease; therapy was well tolerated (36).

SAFETY EXPERIENCE

Adverse events and clinical laboratory data from 315 patients in the five single-agent U.S. studies were combined to provide a safety profile of Rituximab® in patients with low-grade or follicular NHL. The majority of adverse events were infusion-related and occurred with decreasing frequency after the first infusion. The most common infusion-related events were fever (49%), chills (32%), nausea (18%), fatigue (16%), headache (14%), angioedema (13%), pruritus (10%), and occasionally, hypotension (10%) and bronchospasm (8%). During the treatment period (up to 30 days following the last dose), 10% of patients experienced Grade 3 or 4 adverse events, which were primarily infusion-related or hematologic. Thrombocytopenia (<50,000 platelets/mm$^3$) occurred in 1.3% of patients, neutropenia (<1000/mm$^3$) occurred in 1.9%, and anemia (<8 gm/dL) occurred in 1.0%. Although Rituximab® induced B-cell depletion in 70%-80% of patients, abnormally decreased serum immunoglobulins were observed in a minority of patients and the incidence of infection did not appear to be increased.

Hypotension requiring interruption of the Rituximab® infusion occurred in 10% of patients and was Grade 3 or 4 in 1%. Angioedema was reported in 13% of patients and was considered serious in one patient. Bronchospasm occurred in 8% of patients; 2% were treated with bronchodilators. A single report of bronchiolitis obliterans was noted. Most patients experienced no further infusion-related toxicities by the second and subsequent infusions. The percentage of patients reporting adverse events upon retreatment was similar to that reported following the first course (14).

Four patients developed arrhythmias during Rituximab® infusion. One of the four discontinued treatment because of ventricular tachycardia and supraventricular tachycardias. The other three patients experienced trigeminy (N=1) and irregular pulse (N=2) and did not require discontinuation of therapy. Angina was reported during infusion and myocardial infarction occurred four days post-infusion in one subject with a prior history of myocardial infarction.

The overall incidence of adverse events and Grade 3 and 4 adverse events was higher in patients with bulky disease than in patients with non-bulky disease. The incidence of dizziness, neutropenia, thrombocytopenia, myalgia, anemia, and chest pain was higher in patients with lesions >10 cm. The incidence of Grade 3 or 4 neutropenia, anemia, hypotension, and dyspnea was also higher in patients with bulky disease compared with patients with lesions <10 cm (19).

Since FDA approval of Rituximab® for treatment of relapsed or refractory low-grade or follicular NHL in 1997, an estimated 17,000 patients have been treated. In May, 1998, descriptions of eight post-marketing reports of severe infusion-related adverse events associated with the use of Rituximab® that resulted in fatal outcomes were summarized. In seven of the eight fatalities, severe symptoms occurred during the first Rituximab® infusion. The cause of death was not reported or remains unknown for two of the eight cases. Severe respiratory events, including hypoxia, pulmonary infiltrates, or adult respiratory distress syndrome contributed to six of the eight reported deaths. One patient had a pretreatment lymphocyte count of 600,000/mm$^3$; another, a creatinine of 8; a third, a respiratory rate of 40; and a fourth, pancytopenia. Patients with a high tumor burden or with a high number of circulating malignant cells may be at higher risk and these patients should be monitored closely throughout each infusion.

Most of the adverse events recently described were previously observed in Rituximab® clinical studies. One notable exception is an infusion-related syndrome associated with rapid tumor lysis, that was reported in six patients with high numbers of circulating tumor cells (37,38). This syndrome was characterized by fever, rigors, bronchospasm with associated hypoxemia, a rapid decline in peripheral lymphocytes, laboratory evidence of tumor destruction, and transient, severe thrombocytopenia. These patients had diagnoses of B-prolymphocytic leukemia (N=2), chronic lymphocytic leukemia (N=2), mantle-cell lymphoma (N=1), or transformed NHL (N=1); all had elevated circulating lymphocytes, bulky adenopathy, and organomegaly. Although five of these six patients required hospitalization, symptoms resolved and subsequent Rituximab® treatments were well tolerated; the last patient refused further therapy and died of progressive disease two weeks later.

In a separate report of seven patients with CLL and one patient with mantle-cell lymphoma, tumor lysis syndrome was observed after the first Rituximab® infusion in those patients with lymphocyte counts >10×10$^9$L (39).

RADIOIMMUNOTHERAPY WITH $^{90}$YTTRIUM-LABELED ANTI-CD20 ANTIBODY IN COMBINATION WITH RITUXIMAB®

Another therapeutic approach to NHL under evaluation is a radiolabeled anti-CD20 antibody (IDEC-Y2B8) in combination with Rituximab®. IDEC-Y2B8 ($^{90}$Y-ibritumomab tiuxetan) is a murine IgG$_1$ kappa anti-CD20 antibody conjugated to $^{90}$Y via a chelator, MX-DTPA, which is covalently bound to the antibody. Rituximab® (250 mg/m2) is administered prior to IDEC-Y2B8 to deplete peripheral B lymphocytes and improve biodistribution of the radiolabeled antibody.

In a recently reported Phase I/II study (40–42), patients with low-grade NHL (N=34), intermediate-grade NHL (N=14), or mantle-cell lymphoma (N=3) were treated with IDEC-Y2B8. The median age was 60, 71% were male, and 96% were Caucasian. Of 51 patients with relapsed or refractory NHL, 34 (67%) responded to single doses of 0.2, 0.3, or 0.4 mCi/kg of IDEC-Y2B8. The ORR was 82% (28/34) for patients with low-grade or follicular NHL and was 43% (6/14) for patients with intermediate-grade lymphoma. No patients with mantle-cell disease responded.

A Phase III randomized study comparing IDEC-Y2B8 with Rituximab® (375 mg/m$^2$ weekly times 4) for treatment of low-grade follicular or transformed NHL patients is ongoing. Another Phase III trial is also being conducted in patients with relapsed NHL who are refractory to Rituximab®.

SUMMARY

In the absence of curative therapy for NHL, the objective of treatment is to achieve control of the disease for a meaningful duration and provide relief of tumor-related symptoms without undue toxicity. Treatment with Rituximab® is a brief, 22-day outpatient therapy with limited adverse events in most patients. In clinical studies, 50% of evaluable relapsed or chemotherapy refractory low-grade or follicular NHL patients achieved complete or partial responses. These responses were durable without maintenance therapy; the median TTP for responders was 13.2 months and the median DR was 11.6 months in the pivotal study.

Rituximab® is approved as a safe and effective treatment for patients with relapsed low-grade or follicular B-cell NHL. It has significant clinical activity, a novel mechanism of action, and compares favorably with alternative therapies in response rate and response duration. Completion of ongoing studies will verify the role of alternative Rituximab® regimens and Rituximab® in the treatment of other CD20+ B-lymphocyte malignancies.

References

1. Press O, Appelbaum F, Ledbetter J, Martin P, Zarling J, Kidd P, Thomas E. Monoclonal antibody IF5 (anti-CD20) serotherapy of human B-cell lymphomas. *Blood* 1987; 69:584–591.

2. Dillman R. Antibodies as cytotoxic therapy. Journal of Clinical Oncology 1994; 12:1497–1515.
3. Grossbard M, Press O, Appelbaum F, Bernstein I, Nadler L. Monoclonal antibody-based therapies of leukemia and lymphoma. *Blood* 1992; 80:863–878.
4. Reff M, Carner K, Chambers K, Chinn P, Leonard J, Raab R, Newman R, Hanna N, Anderson D. Depletion of B cells in vivo by a chimeric mouse human monoclonal antibody to CD20. *Blood* 1994; 83:435–445.
5. Demidem A, Lam T, Alas S, Hariharan K, Hanna N, Bonavida B. Chimeric anti-CD20 (IDEC-C2B8) monoclonal antibody sensitizes a B cell lymphoma cell line to cell killing by cytotoxic drugs. Cancer Biotherapy & Radiopharmaceuticals 1997; 12:177–186.
6. Maloney D, Liles T, Czerwinski D, Waldichuk C, Rosenberg J, Grillo-López A, Levy R. Phase I clinical trial using escalating single-dose infusion of chimeric anti-CD20 monoclonal antibody (IDEC-C2B8) in patients with recurrent B-cell lymphoma. *Blood* 1994; 84:2457–2466.
7. Maloney D, Grillo-López A, White C, Bodkin D, Schilder R, Neidhart J, Janakiraman N, Foon K, Liles T-M, Dallaire B, Wey K, Royston I, Davis T, Levy R. IDEC-C2B8 (Rituximab®) anti-CD20 monoclonal antibody therapy in patients with relapsed low-grade non-Hodgkin's lymphoma. *Blood* 1997; 90: 2188–2195.
8. McLaughlin P, Grillo-López A, Link B, Levy R, Czuczman M, Williams M, Heyman M, Bence-Bruackler I, White C, Cabanillas F, Jain V, Ho A, Lister J, Wey K, Shen D, Dallaire B. Rituximab® chimeric anti-CD20 monoclonal antibody therapy for relapsed indolent lymphoma: half of patients respond to a 4-dose treatment program. Journal of Clinical Oncology 1998; 16:2825–2833.
9. McLaughlin P, Grillo-López A, Maloney D, Link B, Levy R, Czuczman M, Cabanillas F, Dallaire B, White C. Efficacy controls in long-term follow-up of patients treated with rituximab for relapsed or refractory, low-grade or follicular NHL. *Blood* 1998; 92:414a–415a.
10. Janakiraman N, McLaughlin P, White C, Maloney D, Shen D, Grillo-López A. Rituximab: Correlation between effector cells and clinical activity in NHL. *Blood* 1998; 92 (10 Suppl 1):337a.
11. Berinstein N, Grillo-López A, White C, Bence-Bruckler I, Maloney D, Czuczman M, Green D, Rosenberg J, McLaughlin P, Shen D. Association of serum Rituximab (IDEC-C2B8) concentration and anti-tumor response in the treatment of recurrent low-grade or follicular non-Hodgkin's lymphoma. Annals of Oncology 1998; 9:995–1001.
12. Tobinai K, Kobayashi Y, Narabayashi M, Ogura M, Kagami Y, Morishima Y, Ohtsu T, Igarashi T, Sasaki Y, Kinoshita T, Murate T. Feasibility and pharmacokinetic study of a chimeric anti-CD20 monoclonal antibody (IDEC-C2B8, rituximab) in relapsed B-cell lymphoma. Annals of Oncology 1998; 9:527–534.
13. Piro L, White C, Grillo-López A, Janakiraman N, Saven A, Beck T, Varns C, Shuey S, Czuczrnan M, Lynch J, Kolitz J, Jain V. Extended Rituxan (anti-CD20 monoclonal antibody) therapy for relapsed or refractory low-grade or follicular non-Hodgkin's lymphoma. 1999; Submitted
14. Davis T, White C, Grillo-López A, Velasquez W, Link B, Maloney D, Dillinan R, Williams M, Mohrbacher A, Weaver R, Dowden S, Levy R. Rituximab: First report of a Phase II (PII) trial in NHL patients (pts) with bulky disease. *Blood* 1998; 92 (10 Suppl 1):414a.
15. Byrd J, White C, Thomas S, Veldsquez W, Rosenberg J, Grillo-López A. Rituximab therapy in previously treated Waldenstrom's Macroglobulinemia: Preliminary evidence of activity. *Blood* 1998; 92 (IO Suppl 1): 106(a).
16. O'Brien S, Freireich E, Andreeff M, Lemer S, Keating M. Phase I/III Study of Rituxan in chronic lymphocytic leukemia (CLL). *Blood* 1998; 92: 105a, #431.
17. Venugopal P, Sivararnan S, Huang X, Chopra H, O'Brein T, Jajeh A, Preisler H. Upregulation of CD20 expression in chronic lymphocytic leukemia (CLL) cells by in vitro exposure to cytokines. *Blood* 1998; 10:247a.
18. Flinn I, O'Donnell P, Noga S, Vogelsang G, Grever M, Goodrich A, Abrams R, Marcellus D, Miller C, Jones R, Ambinder R. In vivo purging and adjuvant immunotherapy with Rituximab PBSC transplant for NHL. *Blood* 1998; 92:648a, #2673.
19. Davis T, Levy R, White C, Czuczman M, McLaughlin P, Link B, Varns C, Weaver R, Grillo-López A. Rituximab: Phase II (PII) retreatment (ReRx) study in patients (pts) with low-grade or follicular (LG/F) NHL. *Blood* 1998; 92 (10 Suppl 1):414a.
20. Davis T, Czerwinski D, Levy R. Therapy of B cell lymphoma with anti-CD20 antibodies can result in the loss of CD20 antigen expression. Clinical Cancer Research 1999; 5: In press.
21. Czuczman M, Grillo-López A, White C, Saleh M, Gordon L, LoBuglio F, Jonas C, Klippenstein D, Dallaire B, Varns C. Treatment of patients with low-grade B-cell lymphoma with the combination of chimeric anti-CD20 monoclonal antibody and CHOP chemotherapy. Journal of Clinical Oncology 1999; 17:268–276.
22. White C, Czuczman M, Grillo-López A, White C, Saleh M, Gordon L, LoBuglio A, Jonas C, Alkuzweny B, Dowen S. Rituximab/CHOP chemoimmunotherapy in patients (pts) with low grade lymphoma (LG/F NHL): Progression free survival (PFS) after three years (median) follow-up. Proceedings of ASCO 1999, In press.
23. Wadler S, Schwartz E. Principles in the biomodulation of cytotoxic drugs by interferons. Seminars in Oncology 1992; 19:45–48.
24. Nakamura K, Kubo A, Hosokawa S, Nagaike K, Hashimoto S. Effect of alpha-interferon on anti-alpha-fetoprotein-monoclonal-antibody targeting of hepatoma. Oncology 1993; 50:35–40.
25. Greiner J, Guadagni F, Noguchi P, Pestka S, Colcher D, Fisher P, Schlom J. Recombinant interferon enhances monoclonal antibody-targeting of carcinoma lesions in vivo. Science 1987; 235:895–898.
26. Murray J, Zukiwski A, Mujoo K, Rosenblum M. Recombinant alpha-interferon enhances tumor targeting of an antimelanoma monoclonal antibody in vivo. Journal of Biological Response Modifiers 1990; 9:556–563.
27. Yokota S, Hara H, Luo Y, Seon B. Synergistic potentiation of in vivo antitumor activity of anti-human T-leukemia immunotoxins by recombinant alpha-interferon and daunorubicin. Cancer Research 1990; 50:32–37.
28. Grillo-López A, Dallaire B, Shen C, Varns C, McClure A, Caralli V. Treatment options for patients with relapsed low-grade or follicular lymphoma: The role of IDEC-C2B8. Antibody Imunoconjugates and *Radiopharmaceuticals* 1995; 8:60.
29. Davis T, Maloney D, White C, Grillo-López A, Williams M, Weiner G, Sklenar T, Levy R. Combination immunotherapy of low grade or follicular (LG/F) non-Hodgkin's lymphoma (NHL) with Rituximab and alpha interferon: Interim analysis. Proceedings of the American Society of Clinical Oncology 1998; 17:11 a.
30. Smalley R, Andersen J, Hawkins M, Bhide V, O'Connell M, Oken M, Borden E. Interferon alfa combined with 30. cytotoxic chemotherapy for patients with non-Hodgkin's lymphoma. *New England Journal of Medicine* 1992; 327: 1336–1341.
31. Hagenbeek A, Carde P, Meerwaldt J H, Somers R, Thomas J, De Bock R, Raemaekers J M, van Hoof A, De Wolf-Peeters C, van Glabbeke M. Maintenance of remission with human recombinant interferon alfa-2a in patients with stages In and IV low-grade malignant non-Hodgkin's lymphoma. European Organization for Research and Treatment of Cancer Lymphoma Cooperative Group. *Journal of Clinical Oncology* 1998; 16:41–47.
32. Solal-Céligny P, Lepage E, Brousse N, Tendler C, Brice P, Haioun C, Gabarre J, Pignon B, Tertian G, Bouabdallah R, Rossi J-F, Doyen C, Coiffier B. Doxorubicin-containing regimen with or without interferon alfa-2b for advanced follicular lymphomas: Final analysis of survival and toxicity in the groupe d'etude des lymphomes folliculaires 86 trial. *Journal of Clinical Oncology* 1998; 16:2332–2338.
33. van der Kolk L, Grillo-López A, Gerritsen W, Jonkhoff A, Baars J, van Oers M. Chimeric anti-CD20 monoclonal antibody (rituximab) plus G-CSF in relapsed B-cell lymphoma: A phase I/II clinical trial. *Blood* 1998; 92:241b, #4037.
34. Coiffier B, Haioun C, Ketterer N, Engert A, Tilly H, Ma D, Johnson P, Lister A, Feuring-Buske M, Radford J A, Capdeville R, Diehl V, Reyes F. Rituximab (anti-CD20 monoclonal antibody) for the treatment of patients with relapsing or refractory aggressive lymphoma: a multicenter phase H study. *Blood* 1998; 92:1927–1932.
35. Link B, Grossbard M, Fisher R, Czuczman M, Gilman P, Lowe A, Vose J. Phase II pilot study of the safety and efficacy of rituximab in combination with CHOP chemotherapy in patients with previously untreated- or high-grade NHL. *Proceedings of the American Society of Clinical Oncology* 1998; 17:3a.
36. Tsai, D, Moore H, Porter D, Vaughn D, Luger S, Loh R, Schuster S, Stadtmauer E. Progressive intermediate grade non-Hodgkin's lymphoma after high dose therapy and autologous peripheral stem cell transplantation (PSCT) has a high response rate to Rituximab. *Blood* 1998; 92:415a, #1713.
37. Byrd J, Waselenko J, Maneatis T, Murphy T, Weickum R, Ward F, White C. Rituximab therapy in hematologic malignancy patients with circulating blood tumor cells: Association with increased infusion-related side effects and rapid tumor lysis. *Blood* 1998; 92 (IO Suppl 1): 106a.
38. Jensen M, Winkler U, Manzke O, Diehl V, Engert A. Rapid tumor lysis in a patient with B-cell chronic lymphocytic leukemia and lymphocytosis treated with an anti-CD20 monoclonal antibody (IDEC-C2B8, rituximab). *Annals of Hematology* 1998; 77:89–91.
39. Winkler U, Jensen M, Manzke O, Tesch H, Bohlen H, Diehl V, Engert A. Severe side effects in patients with B-cell chronic lymphocytic leukemia (CLL) and lymphocytosis treated with the monoclonal antibody Rituximab. *Blood* 1998; 92:285b, #4228.
40. Witzig T, White C, Wiseman G, Gordon L, Emmanouilides C, Raubitschek A, Janakiraman N, Gutheil J, Spies S, Silverman D, Parker E, Grillo-López A. Phase I/II trial of IDEC-Y2B8 radioimmunotherapy for treatment of relapsed or refractory CD20 positive B-cell non-Hodgkin's lymphoma. *Journal of Clinical Oncology* 1999; Submitted.
41. Wiseman G, White C, Witzig T, Gordon L, Emmanouilides C, Raubitschek A, Janakiraman N, Spies S, Silverman D, Gutheil J, Schilder R, Parker E, Rosenberg J, Grillo-López A. IDEC-Y2B8 radioimmunotherapy: Baseline bone marrow involvement and platelet count are better predictors of hematologic toxicity than dosimetry. *Blood* 1998; 92:417a.
42. Witzig T, White C, Wiseman G, Gordon L, Emmanouilides C, Raubitschek A, Janakiraman N, Spies S, Silverman D, Gutheil J, Schilder R, Ding E, Shen D, Grillo-López A. IDEC-Y2B8 Radioimmunotherapy: Responses in patients with splenomegaly. *Blood* 1998; 92:417(a).
43. Witherspoon R P, Lum L G, Storb R. Immunologic reconstitution after bone marrow grafting. Semin Hematol 21:2, 1984.
44. Anderson, K C et al. Hematological engraftment and immune reconstitution posttransplant with anti-B1 purged autologous bone marrow. *Blood* 69:597, 1987.
45. Lum L G. Kinetics of immune reconstitution after human marrow transplantation. Blood 69:369, 1987.
46. Azogui O., Gluckman E., Fradelizi, D., Inhihibition of IL-2 production after human allogeneic bone marrow transplantation. J. Immunol. 131:1205, 1983
47. Welte, K. et al, Defective Interleukin-2 production in patients after bone marrow transplantation and in vitro restoration of defective T lymphocite proliferation by highly purified Interleukin. Blood 64:380, 1984.
48. Cayeau, S. et al., T-cell ontogeny after bone marrow transplantation: failure to synthesize lnterleukin-2 (IL-2) and lack of CD2- and CD3-mediated proliferation by both CDE4+ and CD8+ cells even in the presence of exogenous IL-2. Blood 74:2270, 1989.
49. Bosley, A. et al., Interleukin-2 as consolidative immuotherapy against minimal residual disease. Nouv Rev Fr Hematol 32:13, 1990.
50. Caligiuri, M. A. et al, Extended continuous infusion low-dose recombinant Interleukin-2 in advanced cancer. Prolonged immunomodulation without significant toxicity. J Clin Oncol 9:2110, 1991.
51. Caligiuri, M. A. et al, Selective immune modulation of NK cells following prolonged infusions of low dose recombinant IL-2. J Clin Invest 91:123, 1993.
52. Caligiuri, M. A., Low-dose reocmbinant Interleukin-2 therapy: rationale and potential clinical applications. SEM in Oncol 20:3, 1993.
53. Klarnet, J. P. et al, Antigen-driven T cell clones can proliferate in vivo, eradicate disseminated leukemia and provide specific immunologic memory. J Immunol. 138:4012, 1987.
54. Soiffer, R. J. et al, Clinical and immunologic effects of prolonged infusion of low-doe recombinant Interleukin-2 after autologous and T cell-depleted allogeneic bone marrow transplantation. Blood 79:517, 1992.
55. Soiffer, R. J. et al, Effect of low-dose Interleukin-2 on disease relapse after T-cell depleted allogeneic bone marrow transplantation. Blood 84:964, 1994.
56. Lauria, F. et al, Immunologic and clinical modifications following low-dose subcutaneous administration of rIL-2 in non-Hodgkin's lymphoma patients after autologous bone marrow transplantation. BMT 18:79, 1996.
57. Vey, N. et al, A pilot study of autologous bone marrow transplantation followed by recombinant Interleukin-2 in malignant lymphomas. Leukemia & Lymphoma 21:107, 1996.
58. Venugopal, P. et al, Upregulation of CD20 expression in CLL cells by cytokines. Submitted to ASH Meeting, December 1998.

What is claimed:

1. A method for reducing residual CD20+ tumor cells in bone marrow or stem cell tissue after myeloablative therapy in a subject in need of such treatment by administering an amount of a non-radiolabeled anti-CD20 antibody effective to reduce the number of residual CD20+ tumor cells in said bone marrow or stem cell tissue.

2. The method of claim 1 wherein said anti-CD20+ antibody comprises human IgG1 constant regions.

3. The method of claim 1 wherein said antibody is a chimeric anti-CD20 antibody.

4. The method of claim 3 wherein said antibody is C2B8.

5. The method of myeloablative claim 1 wherein the treated subject had B cell lymphoma.

6. The method of claim 5 wherein said B cell lymphoma is selected from the group consisting of low grade/follicular non-Hodgkin's lymphoma (NHL), small lymphocytic (SL) NHL, intermediate grade/follicular NHL, intermediate grade diffuse NHL, chronic lymphocytic leukemia (CLL), high grade immunoblastic NHL, high grade lymphoblastic NHL, high grade small non-cleaved cell NHL, bulky disease NHL, mantle cell lymphoma, AIDS-related lymphoma and Waldenstrom's Macroglobulinemia.

7. The method of claim 3 wherein the treated subject has low grade, intermediate grade or high-grade lymphoma.

8. The method of claim 3 wherein the treated subject has stage I, stage II, stage III or stage IV non-Hodgkin's lymphoma.

9. The method of claim 3 wherein myeloablative therapy is effected using Y2B8.

10. The method of claim 3 wherein the treated subject has relapsed after myeloablative therapy.

11. The method of claim 1, further comprising administering at least one chemotherapeutic agent.

12. The method of claim 2 wherein the anti-CD20 antibody is C2B8 which is administered at a dosage ranging from 10–500 mg/m$^2$.

13. The method of claim 12 wherein the antibody is administered by infusion.

14. The method of claim 12 wherein at a dosage of about 375 mg/m$^2$.

15. The method of claim 14 wherein said antibody dosage is administered weekly.

* * * * *